US 10,485,477 B1

United States Patent
Lapetina et al.

(10) Patent No.: US 10,485,477 B1
(45) Date of Patent: Nov. 26, 2019

(54) EXTENSIBLE WRIST BAND FOR WEARABLE DEVICE

(71) Applicant: Verily Life Sciences LLC, Mountain View, CA (US)

(72) Inventors: John Lapetina, Los Altos Hills, CA (US); Russell Norman Mirov, Los Altos, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 566 days.

(21) Appl. No.: 14/303,073

(22) Filed: Jun. 12, 2014

(51) Int. Cl.
*A61B 5/00* (2006.01)
*A61B 5/11* (2006.01)

(52) U.S. Cl.
CPC ............ *A61B 5/681* (2013.01); *A61B 5/0002* (2013.01); *A61B 5/1112* (2013.01); *A61B 5/4824* (2013.01); *A61B 5/742* (2013.01); *A61B 5/7475* (2013.01)

(58) Field of Classification Search
CPC ..... A61B 5/0002; A61B 5/4824; A61B 5/681; A61B 5/1112
See application file for complete search history.

(56) References Cited

U.S. PATENT DOCUMENTS

| 5,883,576 A | 3/1999 | De La Huerga |
| 6,619,835 B2 | 9/2003 | Kita |
| 7,946,758 B2 | 5/2011 | Mooring |
| 2012/0194976 A1* | 8/2012 | Golko ...................... G06F 1/163 361/679.01 |
| 2012/0253485 A1* | 10/2012 | Weast ...................... G06F 1/163 700/91 |
| 2013/0120106 A1* | 5/2013 | Cauwels ................. G06F 1/163 340/3.1 |
| 2014/0070957 A1* | 3/2014 | Longinotti-Buitoni ...................... A61B 5/6804 340/870.01 |
| 2014/0107493 A1* | 4/2014 | Yuen ...................... H04W 4/027 600/473 |
| 2015/0054654 A1* | 2/2015 | Albinali ................. G08B 21/02 340/870.01 |
| 2015/0345985 A1* | 12/2015 | Fung ....................... G01P 15/02 702/160 |

* cited by examiner

*Primary Examiner* — Christopher Koharski
*Assistant Examiner* — Amanda L Steinberg
(74) *Attorney, Agent, or Firm* — McDonnell Boehnen Hulbert & Berghoff LLP

(57) ABSTRACT

A wearable device includes a strap configured for removable placement about an external body surface. The wearable device also includes an electronics module having a communication port. The wearable device further includes a biological sensor coupled to the electronics module and configured to obtain a measurement via the external body surface. The wearable device also includes a holder coupled to the strap. The holder defines a frame configured to receive the electronics module, and the frame defines an opening through which the biological sensor is able to obtain the measurement via the external body surface. The wearable device further includes a flexible printed circuit board (PCB) embedded within at least one of the holder or the strap. The wearable device also includes a connector configured to electrically connect the flexible PCB to the communication port.

13 Claims, 12 Drawing Sheets

700

702 — SECURING AN ELECTRONICS MODULE WITHIN A HOLDER COUPLED TO A STRAP TO FORM A WEARABLE DEVICE, WHERE: (I) THE STRAP IS CONFIGURED FOR REMOVABLE PLACEMENT ABOUT AN EXTERNAL BODY SURFACE, (II) THE ELECTRONICS MODULE INCLUDES A COMMUNICATION PORT, (III) THE ELECTRONICS MODULE INCLUDES A BIOLOGICAL SENSOR CONFIGURED TO OBTAIN A MEASUREMENT VIA THE EXTERNAL BODY SURFACE, (IV) THE HOLDER DEFINES A FRAME CONFIGURED TO RECEIVE THE ELECTRONICS MODULE, (V) THE FRAME DEFINES AN OPENING THROUGH WHICH THE BIOLOGICAL SENSOR CAN OBTAIN THE MEASUREMENT VIA THE EXTERNAL BODY SURFACE, (VI) AT LEAST ONE OF THE STRAP AND THE HOLDER INCLUDES A FLEXIBLE PRINTED CIRCUIT BOARD (PCB), (VII) THE FLEXIBLE PCB INCLUDES A CONNECTOR, AND WHEREIN SECURING THE ELECTRONICS MODULE WITHIN THE HOLDER COMPRISES ELECTRICALLY CONNECTING THE FLEXIBLE PCB TO THE COMMUNICATION PORT BY WAY OF THE CONNECTOR

704 — MOUNTING THE WEARABLE DEVICE TO THE WRIST SUCH THAT THE OPENING IS OVER THE EXTERNAL BODY SURFACE

706 — CAUSING THE BIOLOGICAL SENSOR TO OBTAIN ONE OR MORE MEASUREMENTS VIA THE EXTERNAL BODY SURFACE

708 — RECEIVING, FROM THE WEARABLE DEVICE, A USER-DISCERNIBLE INDICATION OF THE ONE OR MORE MEASUREMENTS

EXTENSIBLE WRIST BAND FOR WEARABLE DEVICE

BACKGROUND

Unless otherwise indicated herein, the materials described in this section are not prior art to the claims in this application and are not admitted to be prior art by inclusion in this section.

Wearable devices may be used to obtain information about the wearer's physical activity and/or health state. For example, a wearable device may include one or more motion sensors, such as an accelerometer or gyroscope, in order to detect movements of the wearer and determine the wearer's level of physical activity (e.g., in terms of steps taken or calories burned). Alternatively or additionally, a wearable device may include one or more biological sensors that measure biological parameters of the wearer. The measured biological parameters could include pulse rate, blood oxygenation (oximetry), blood pressure, skin temperature, galvanic skin response (GSR), or other parameters that may relate to the wearer's level of physical exertion.

SUMMARY

The present disclosure describes embodiments that relate to an extensible wrist band for a wearable device. In one aspect, the present application describes a wearable device. The wearable device includes a strap configured for removable placement about an external body surface. The wearable device also includes an electronics module having a communication port. The wearable device further includes a biological sensor coupled to the electronics module and configured to obtain a measurement via the external body surface. The wearable device also includes a holder coupled to the strap. The holder defines a frame configured to receive the electronics module, and the frame defines an opening through which the biological sensor is able to obtain the measurement via the external body surface. The wearable device further includes a flexible printed circuit board embedded within at least one of the holder or the strap. The wearable device also includes a connector configured to electrically connect the flexible PCB to the communication port when the electronics module is received in the frame.

In another aspect, the present disclosure describes a method. The method includes securing an electronics module within a holder coupled to a strap to form a wearable device. The strap is configured for removable placement about an external body surface. The electronics module includes a communication port. The electronics module also includes a biological sensor configured to obtain a measurement via the external body surface. The holder defines a frame configured to receive the electronics module, and the frame defines an opening through which the biological sensor can obtain the measurement via the external body surface. At least one of the strap and the holder includes a flexible printed circuit board (PCB), where the flexible PCB includes a connector. Securing the electronics module within the holder comprises electrically connecting the flexible PCB to the communication port by way of the connector. The method also includes mounting the wearable device to the external body surface such that the opening is over the external body surface. The method further includes causing the biological sensor to obtain one or more measurements via the external body surface. The method also includes receiving, from the wearable device, a user-discernible indication of the one or more measurement.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE FIGURES

FIG. 7 is a flow chart of a method of using a wearable device, in accordance with an example embodiment.

DETAILED DESCRIPTION

The following detailed description describes various features and functions of the disclosed systems and methods with reference to the accompanying figures. In the figures, similar symbols identify similar components, unless context dictates otherwise. The illustrative system and method embodiments described herein are not meant to be limiting. It may be readily understood that certain aspects of the disclosed systems and methods can be arranged and combined in a wide variety of different configurations, all of which are contemplated herein.

I. OVERVIEW

A body-mountable or wearable device may be configured to measure one or more physiological parameters of the wearer. The wearable device may have a modular design where the wearable device includes a core electronics module that can be removably secured within a separate wrist band module.

In an example, the electronics module may include a biological sensor, a processor, a display, and a battery. The wrist band may add functionality to the electronics module. For example, the wrist band may include buttons, additional biological sensors, an antenna, another display, touch sensors, microphones, and an additional battery. In an example, the additional battery may be configured to power the electronics module when a battery of the core electronics module is depleted. Thus, the electronics module may include basic functionality that might be extended or enhanced by coupling the electronics module to the wrist band.

Furthermore, such modular configuration allows for coupling different wrist bands to the same electronics module. For example, the electronics module may be plugged into different types of wrist bands, each wristband having a different functionality. For instance, one wrist band may be appropriate for exercise and may be configured to measure a galvanic skin response, which may be related to perspiration and, thus, the wearer's activity level (e.g., heart rate). As another example, a wrist band may be configured to include a biological sensor operable to measure glucose levels. Some wrist bands may be non-electrical and may be used to bring the electronics module into contact with the skin of a wearer. Thus, different wrist bands could provide the user with different functions.

II. EXAMPLE WEARABLE DEVICES

Figure 1:
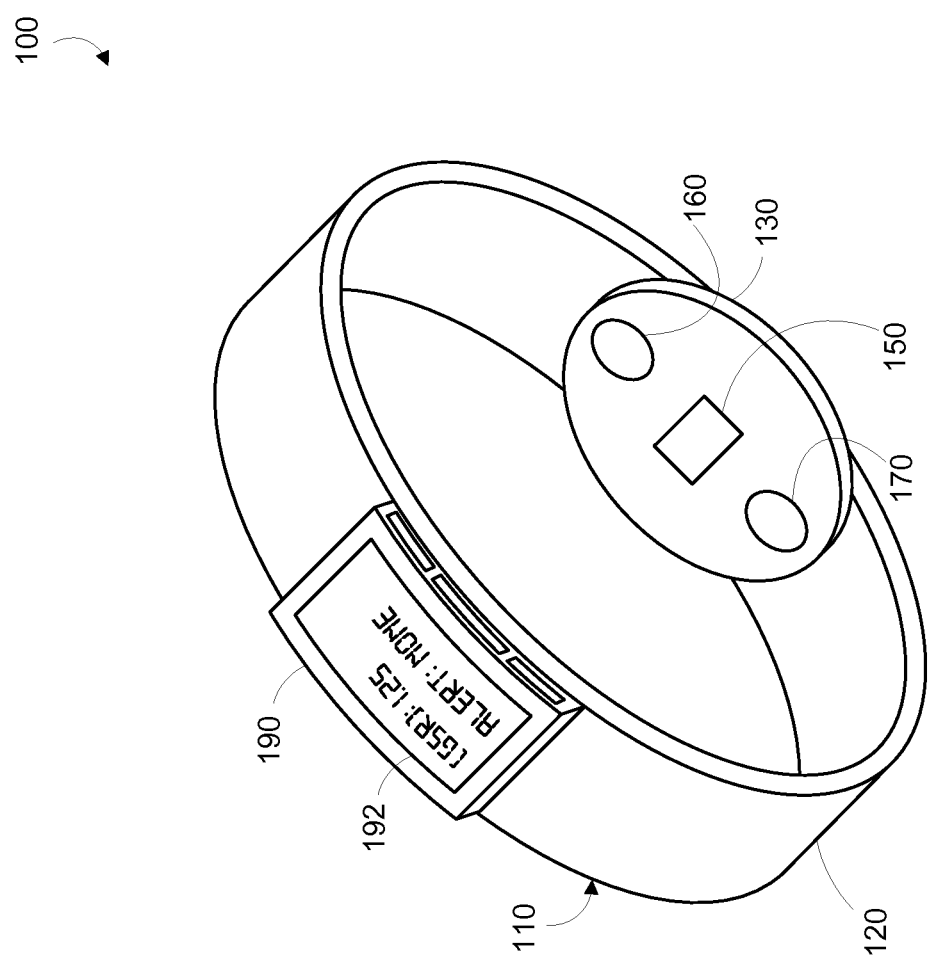
FIG. 1 is a perspective view of an example wearable device, in accordance with an example embodiment.

A wearable device 100 can be configured to measure a Galvanic skin resistance (GSR) of skin at an external body surface proximate to the wearable device 100. The wearable device 100 can also be configured to be powered by a rechargeable battery disposed in the wearable device 100. The term "wearable device," as used in this disclosure, refers to any device that is capable of being worn at, on or in proximity to an external body surface, such as a wrist, ankle, waist, chest, or other body part. A mount 110, such as a belt, wristband, ankle band, etc. can be provided to mount the device at, on or in proximity to the external body surface. In some embodiments, a mount could additionally or alternatively include an adhesive. For example, a mount could include and adhesive and could be configured such that it could be used to mount a wearable device to an external body surface of a wearer without wrapping around a part of the wearer (e.g., a limb). The mount 110 may prevent the wearable device 100 from moving relative to the body to ensure consistent contact between the wearable device 100 and the skin to enable consistent measurement of the GSR of the skin. In one example, shown in FIG. 1, the mount 110, may take the form of a strap or band 120 that can be worn around a part of the body.

A housing 130 is disposed on the mount 110 such that the housing 130 can be positioned on an external surface of the body. In this position, a first electrical contact 160 and a second 170 electrical contact protruding from the housing 130 could contact skin at the external surface of the body such that the GSR of the skin at the external surface of the body could be measured between the first and second electrical contacts 160, 170. The first and second electrical contacts 160, 170 could be configured to interface with a charger or other device such that a rechargeable battery that powers the wearable device 100 could be charged through the first and second electrical contacts 160, 170.

The first and second electrical contacts 160, 170 could be composed of an electrically conductive material, such as a metal or a combination of metals, or a nonmetal conductor. The first electrical contact 160 and second electrical contact 170 could be composed of the same material or different materials. The first and second electrical contacts 160, 170 could each be composed of a single material or could be composed of multiple materials. For example, the electrical contacts 160, 170 could have a bulk composed of one material and a surface plating of another material. For example, the electrical contacts 160, 170, could have a bulk composed of copper and a surface composed of gold or of gold alloyed with nickel and/or cobalt. The surface layer could be deposited by a number of methods familiar to one skilled in the art; for example, electroplating. Other compositions are possible, as well.

The first and second electrical contacts 160, 170 could be spring loaded. That is, the electrical contacts 160, 170 could be configured to include one or more springs or other elements that could be reversibly compressed. The electrical contacts 160, 170 could be spring loaded in a direction perpendicular to an external surface of the body to which the housing 130 could be mounted. That is, the electrical contacts 160, 170 could be spring loaded in order to improve and/or make more consistent an electrical connection between the electrical contacts 160, 170 and skin of the external body surface to which the housing 130 was mounted by the mount 110. Alternatively, first and second electrical contacts 160, 170 could be fixed relative to housing 130.

The geometry of the aspects of the electrical contacts 160, 170 that protrude from the housing 130 could be configured to improve and/or make more consistent an electrical connection between the electrical contacts 160, 170 and skin of the external body surface to which the housing 130 was mounted by the mount 110. For example, the protruding aspects of the electrical contacts 160, 170 could be hemispherical, conical, parabolic, cylindrical, or shaped in some other manner. The electrical contacts 160, 170 could be flat or substantially flat plates (e.g., rectangular, triangular, or other-shaped plates protruding from the housing 130). The electrical contacts 160, 170 could have a faceted geometry. For example, the electrical contacts 160, 170 could be triangular, rectangular, or other-shapes pyramids. The protruding aspects of the electrical contacts 160, 170 could have, for example, a characteristic size (e.g., diameter of cylinders, cones, or hemispheres, width of rectangular prisms or plates, or some other measure of size) between 1 and 5 millimeters. Further, the protruding aspects of the electrical contacts 160, 170 could have an inscribed, cast, and/or pressed texture or pattern. Additionally or alternatively, the exposed aspects of the electrical contacts 160, 170 could be roughened mechanically, chemically, or by some other method. Other geometries, sizes, surface treatments, and other aspects of the configuration of the electrical contacts 160, 170 are anticipated.

The electrical contacts 160, 170 could be arranged a distance apart such that a GSR measured using the electrical contacts 160, 170 could have a desired property or properties. For example, the electrical contacts 160, 170 could be separated by a distance of between 1 and 50 millimeters, such as about 25 millimeters. The electrical contacts 160, 170 could be disposed on the housing 130 such that, if the housing 130 is mounted to a wrist of a wearer of the wearable device 100, the electrical contacts 160, 170 would be arranged on a line substantially parallel to the bones of the forearm of the wearer (i.e., the humerus and ulna). Other distances and directions are also possible.

The housing 130 could be configured to be water-resistant. That is, the housing could be configured to include sealants, adhesives, gaskets, welds, press-fitted seams, and/or other joints such that the housing 130 was resistant to water entering an internal volume or volumes of the housing 130. Further, the interface between the housing 130 and the first and second electrical contacts 160, 170 protruding from the housing 130 could be configured such that the combination of the housing 130 and the electrical contacts 160, 170 is water-resistant.

The wearable device 100 includes electronics (not shown in FIG. 1) configured to measure a Galvanic skin resistance (GSR) of the skin at an external surface of the body proximate to the housing 130, using the first and second electrical contacts 160, 170 when the wearable device 100 is mounted to the external surface of the body. The electronics may include a GSR sensor configured to obtain a measurement relating to the GSR of the skin at the external surface of the body, via the first and second electrical contacts 160, 170, when a rectifier disposed in the wearable device 100 is reverse biased. The GSR sensor could include a reference voltage source electrically connected to the first electrical contact 160 through a resistor having a reference resistance. The GSR sensor may also include a voltage sensor electrically connected to the first electrical contact 160. The reference voltage source generates a reference voltage relative to the second electrical contact 170 and the voltage sensor measures a voltage between the first electrical contact 160 and the second electrical contact 170. A battery recharger could also be included in the electronics and electrically connected to the first electrical contact 160 through the rectifier.

A GSR of skin proximate to the electrical contacts 160, 170 could be determined based on a measurement relating to the GSR of the skin obtained using the GSR sensor when the wearable device 100 is mounted to the external surface of the body and when the rectifier is reverse biased. In some examples, the measurement relating to the GSR of the skin could include a measurement of the voltage between the first and second electrical contacts 160, 170, and the GSR of skin proximate to the electrical contacts 160, 170 could be determined based on the measured voltage, the value of a reference voltage produced by a reference voltage source, a resistance of a reference resistor, and/or other factors. For example, the GSR could be determined by calculating a multiple of the reference resistance corresponding to the measured voltage divided by a difference, where the difference is the measured voltage subtracted from the reference voltage. Other methods of determining a GSR could be used, for example a lookup table relating measured voltages to GSR values.

The electrical contacts 160, 170 protruding from the housing 130 could additionally be used for other purposes. For example, electronics disposed in the wearable device 100 could be used to sense an electrocardiogram (ECG) signal, a Galvanic skin potential (GSP), an electromyogram (EMG) signal, and/or some other physiological signal present at the electrical contacts 160, 170. Additionally or alternatively, the electrical contacts 160, 170 could be used to detect the presence of a charging device or some other electronic system electrically connected to the electrical contacts 160, 170.

In some examples, the housing 130 further includes at least one detector 150 for detecting at least one other physiological parameter, which could include any parameters that may relate to the health of the person wearing the wearable device. For example, the detector 150 could be configured to measure blood pressure, pulse rate, respiration rate, skin temperature, etc. At least one of the detectors 150 could be configured to non-invasively measure one or more targets in blood circulating in subsurface vasculature proximate to the wearable device. In a non-exhaustive list, detector 150 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor.

The wearable device 100 may also include a user interface 190 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 190 may include a display 192 where a visual indication of the alert or recommendation may be displayed. The display 192 may further be configured to provide an indication the battery status of the device or an indication of any measured physiological parameters, for instance, the GSR being measured by the device.

Figure 2A:
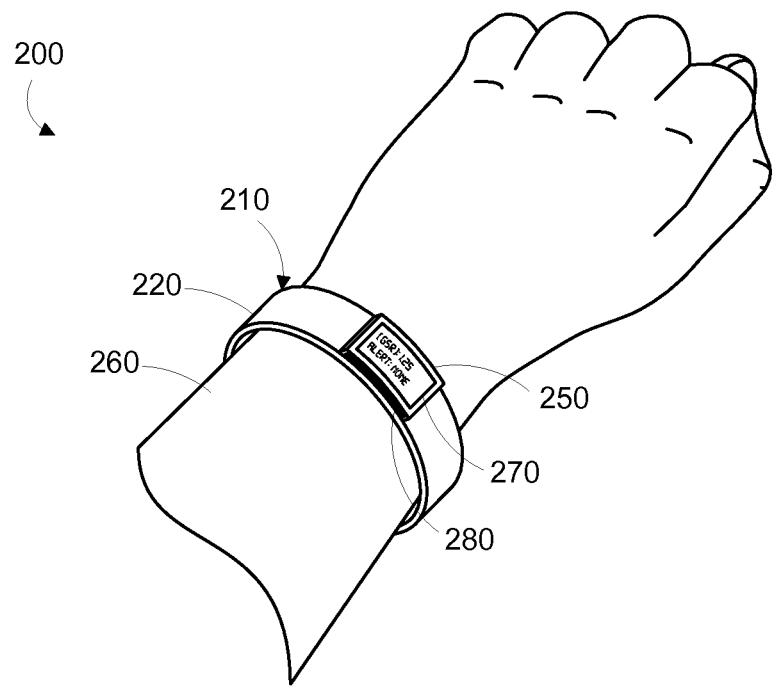
FIG. 2A is a perspective top view of an example wrist-mountable device, when mounted on a wearer's wrist, in accordance with an example embodiment.
Figure 2B:
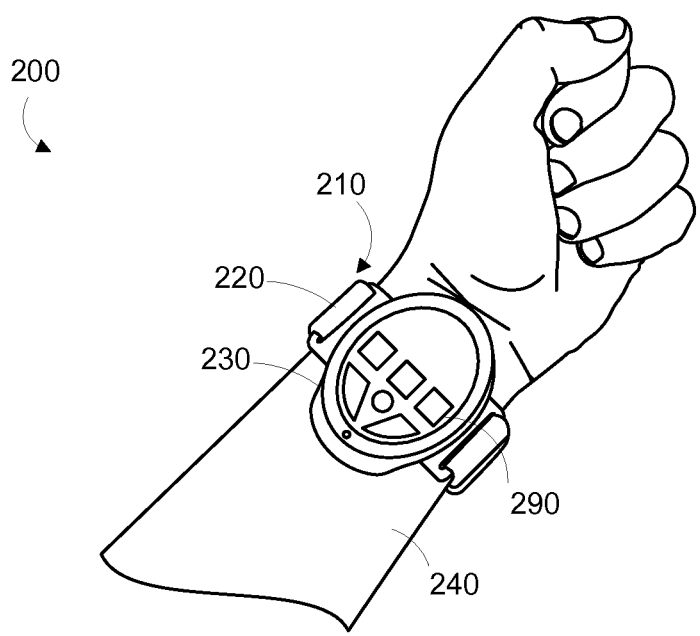
FIG. 2B is a perspective bottom view of the example wrist-mountable device shown in FIG. 2A, when mounted on a wearer's wrist, in accordance with an example embodiment.

In some examples, the wearable device is provided as a wrist-mounted device, as shown in FIGS. 2A, 2B, 3A-3C, 4A, 4B, and 5A-5E. The wrist-mounted device may be mounted to the wrist of a living subject with a wristband or cuff, similar to a watch or bracelet. As shown in FIGS. 2A and 2B, the wrist mounted device 200 may include a mount 210 in the form of a wristband 220, a housing 230 positioned on the anterior side 240 of the wearer's wrist, and a user interface 250 positioned on the posterior side 260 of the wearer's wrist. The wearer of the device may receive, via the user interface 250, one or more recommendations or alerts generated either from a remote server or other remote computing device, or alerts generated by the operation of the wrist mounted device 200 (for example, alerts related to a GSR measured by the wrist mounted device 200). Such a configuration may be perceived as natural for the wearer of the device in that it is common for the posterior side 260 of the wrist to be observed, such as the act of checking a wrist-watch. Accordingly, the wearer may easily view a display 270 on the user interface. Further, the housing 230 may be located on the anterior side 240 of the wearer's wrist. However, other configurations are contemplated.

The display 270 may be configured to display a visual indication of the alert or recommendation and/or an indication of the status of the wearable device or an indication of measured physiological parameters, for instance, the GSR of the skin being measured by the wrist mounted device 200. Further, the user interface 250 may include one or more buttons 280 for accepting inputs from the wearer. For example, the buttons 280 may be configured to change the text or other information visible on the display 270. As shown in FIG. 2B, housing 230 may also include one or more buttons 290 for accepting inputs from the wearer. The buttons 290 may be configured to accept inputs for controlling aspects of the wrist mounted device 200, such as initiating a GSR measurement period, or inputs indicating the wearer's current health and/or affect state (i.e., normal, anxious, angry, calm, migraine, shortness of breath, heart attack, fever, "flu-like" symptoms, food poisoning, etc.).

Figure 3A:
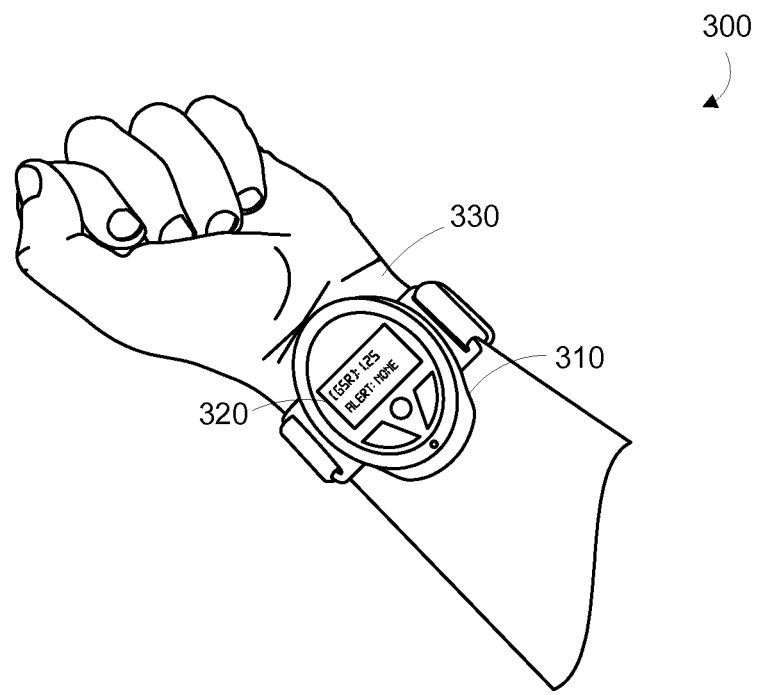
FIG. 3A is a perspective bottom view of an example wrist-mountable device, when mounted on a wearer's wrist, in accordance with an example embodiment.
Figure 3B:
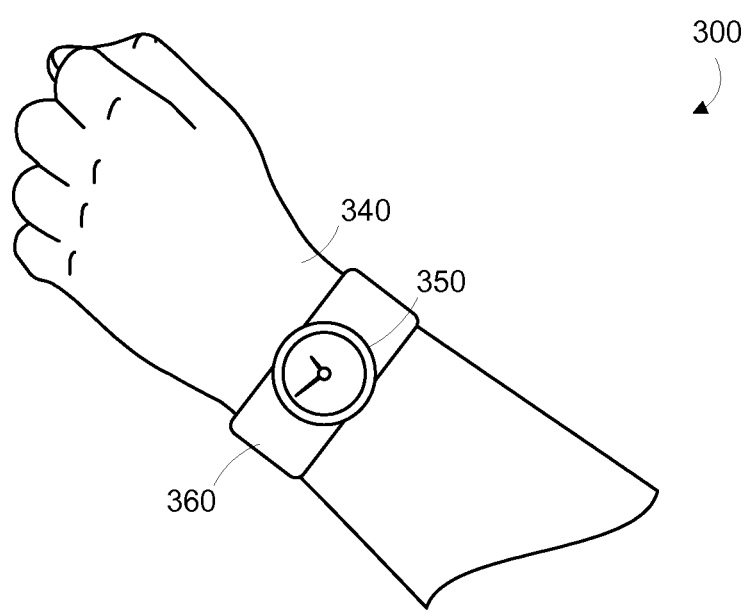
FIG. 3B is a perspective top view of the example wrist-mountable device shown in FIG. 3A, when mounted on a wearer's wrist, in accordance with an example embodiment.
Figure 3C:
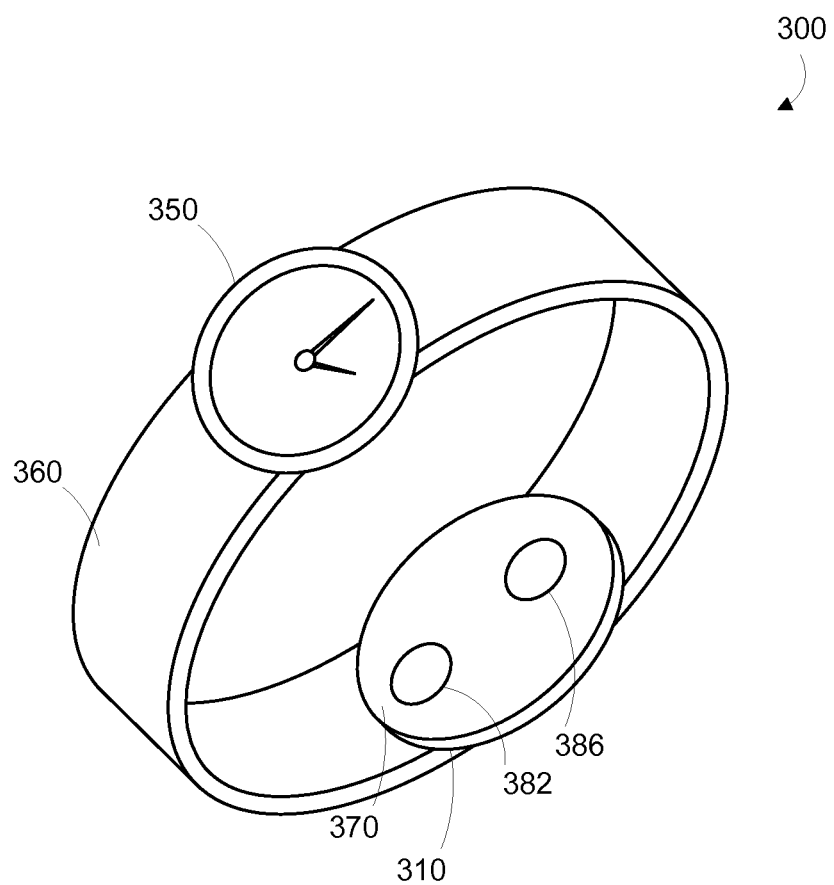
FIG. 3C is a perspective view of the example wrist-mountable device shown in FIGS. 3A and 3B, in accordance with an example embodiment.

In another example wrist-mounted device 300, shown in FIGS. 3A-3C, the housing 310 and user interface 320 are both provided on the same side of the wearer's wrist, in particular, the anterior side 330 of the wrist. On the posterior side 340, a watch face 350 may be disposed on the strap 360. While an analog watch is depicted in FIG. 3B, one of ordinary skill in the art will recognize that any type of clock may be provided, such as a digital clock.

As can be seen in FIG. 3C, the inner face 370 of the housing 310 is intended to be worn proximate to skin on an external surface of the wearer's body. A first electrical contact 382 and a second electrical contact 386 protrude from the inner face 370 of the housing 310 such that a measurement of the GSR of skin proximate to the inner face 370 could be measured using the electrical contacts 382, 386 when the wrist-mounted device 300 was mounted to a wrist of a wearer. The electrical contacts 382, 386 could also be used to charge a battery of the wrist-mounted device 300.

Figure 4A:
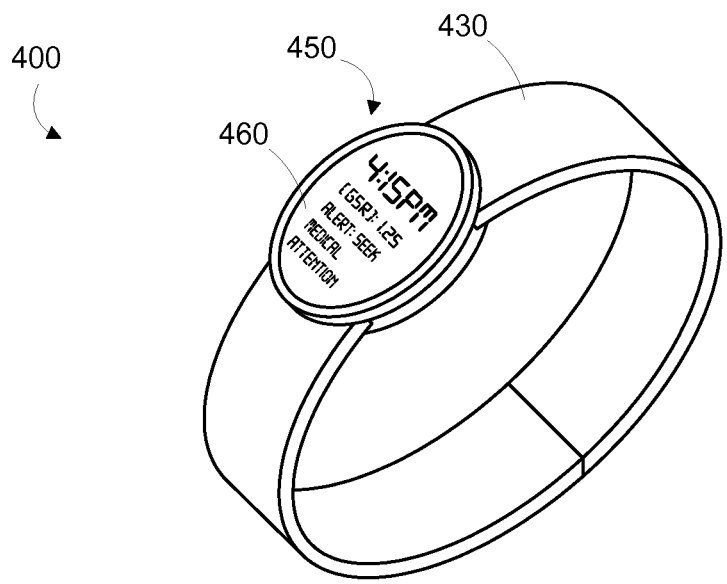
FIG. 4A is a perspective view of an example wrist-mountable device, in accordance with an example embodiment.
Figure 4B:
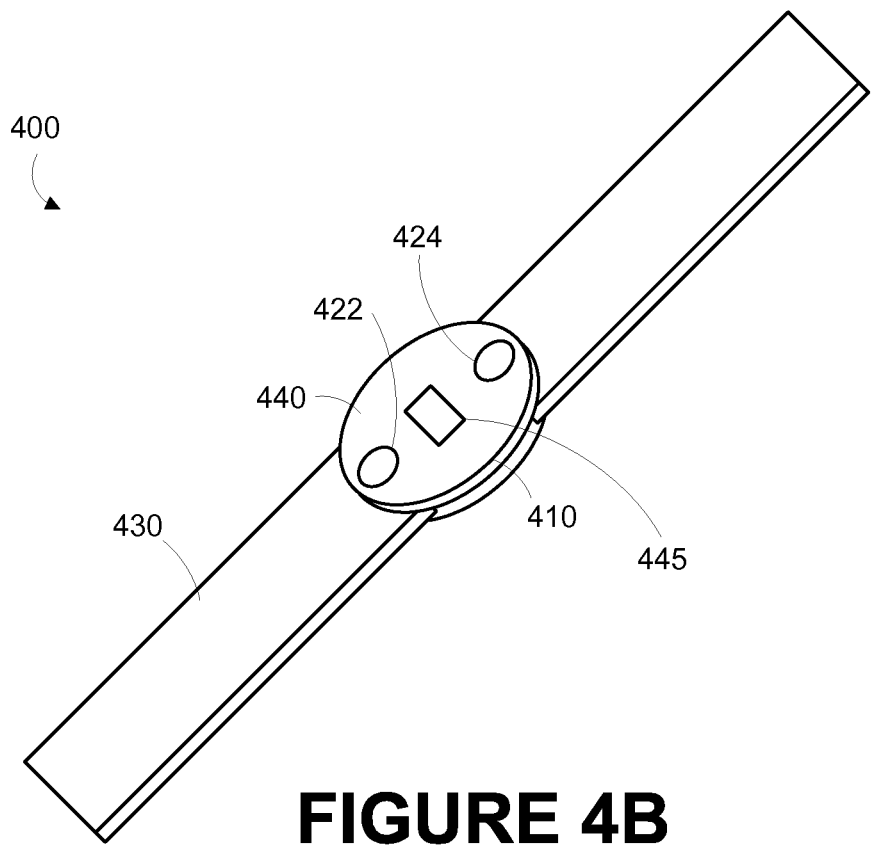
FIG. 4B is a perspective bottom view of the example wrist-mountable device shown in FIG. 4A, in accordance with an example embodiment.

In a further example shown in FIGS. 4A and 4B, a wrist mounted device 400 includes a housing 410, disposed on a strap 430. Inner face 440 of housing 410 may be positioned proximate to a body surface so that a first electrical contact 422 and a second electrical contact 424 protruding from the housing 410 may be used to measure the Galvanic skin resistance (GSR) of skin of the body surface proximate to the housing 410. A detector 445 for detecting at least one other physiological parameter of the wearer could also be disposed on the inner face 440 of the housing 410. A user interface 450 with a display 460 may be positioned facing outward from the housing 410. As described above in connection with other embodiments, user interface 450 may be configured to display data about the wrist mounted device 400, including whether the wrist mounted device 400 is active, a GSR of skin proximate to the inner face 440 of the housing 410 measured using the first and second electrical contacts 422, 424, physiological data about the wearer obtained using the detector 445, and one or more alerts generated by a remote server or other remote computing device, or a processor located on the wrist mounted device 400. The user interface 450 may also be configured to display the time of day, date, or other information that may be relevant to the wearer.

III. EXAMPLE EXTENSIBLE WEARABLE DEVICE

In examples, a wearable device such as any of the wearable devices described above may be designed modularly such that the wearable device includes an electronics module that can be coupled to a variety of wrist bands. Different wrist bands may have different functionalities and may extend the capability of the electronics module in different ways. For example, the electronics module may include a biological sensor, a processor, a display, and a battery. One wrist band may be appropriate for exercise monitoring. The wrist band may, for instance, and may be configured to measure a galvanic skin response, which may be related to perspiration and, thus, the wearer's activity level (e.g., heart rate). Another wrist band may be configured to include a biological sensor operable to measure glucose levels. Other examples include a pulse rate sensor, a blood pressure sensor, a skin temperature sensor, a blood oxygenation sensor, etc. In this manner, the electronics module may have basic functionality that can be extended by coupling the electronics module to a variety of different wrist bands.

Figure 5A:
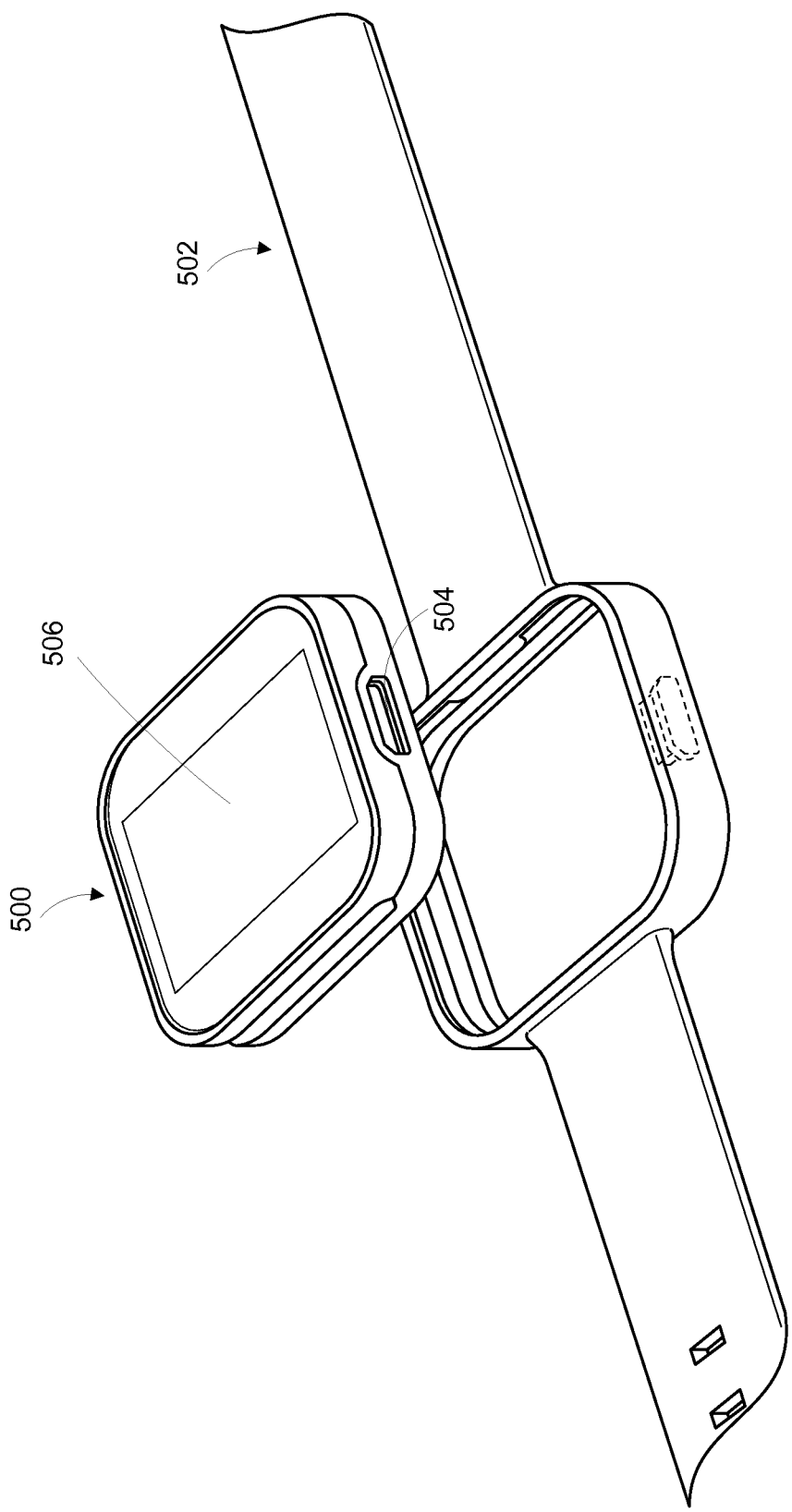
FIG. 5A illustrates an example extensible wearable device, in accordance with an example embodiment.

FIG. 5A illustrates an example extensible wearable device, in accordance with an example embodiment. FIG. 5A depicts an electronics module 500 and a wrist band 502. The electronics module 500 may include a communication port 504. The electronics module 500 may also include a display (e.g., a touch screen) 506. In examples, the electronics module 500 may include one or more biological sensors (not shown) configured to, for example, measure Galvanic skin resistance or any other biological/physiological parameters via an external body surface proximate to a wrist of a user when the wearable device is worn.

To measure a given parameter, the electronics module 500 may include two electrical contacts that contact the wearer's skin at a location such as the wearer's wrist when the wearable device is worn. With the electrical contacts against the wearer's skin, for example, electronic components within the electronics module 500 the device may be used to measure an external resistance between the first and second electrical contacts. This external resistance is related to the wearer's Galvanic skin resistance. In another example, the biological sensor could measure parameters optically. For instance, the sensor may be configured to use visible or infrared light. In this case, the sensor may include light-emitting diode (LED) and a light sensor, for example.

The electronics module 500 may include a user-interface that comprises, for example, the display 506. The user-interface may be configured to provide a user-discernible indication of measurements obtained by the biological sensor coupled to the electronics module 500. The electronics module 500 may be powered by a rechargeable battery embedded within the electronics module 500. In examples, the electronics module 500 may include one or more sensors such as an accelerometer, a gyroscope, a location sensor, any type of motion sensors, etc.

The electronics module may further include at least one processor and data storage. The data storage may, for example, be configured to store sensor measurements. The data storage may also be configured to store program instructions that, when executed by the at least one processor, implement several functionalities associated with making sensor measurements, communication with other devices and servers, providing indications through the user interface, and any other functionalities contemplated herein.

Figure 5B:
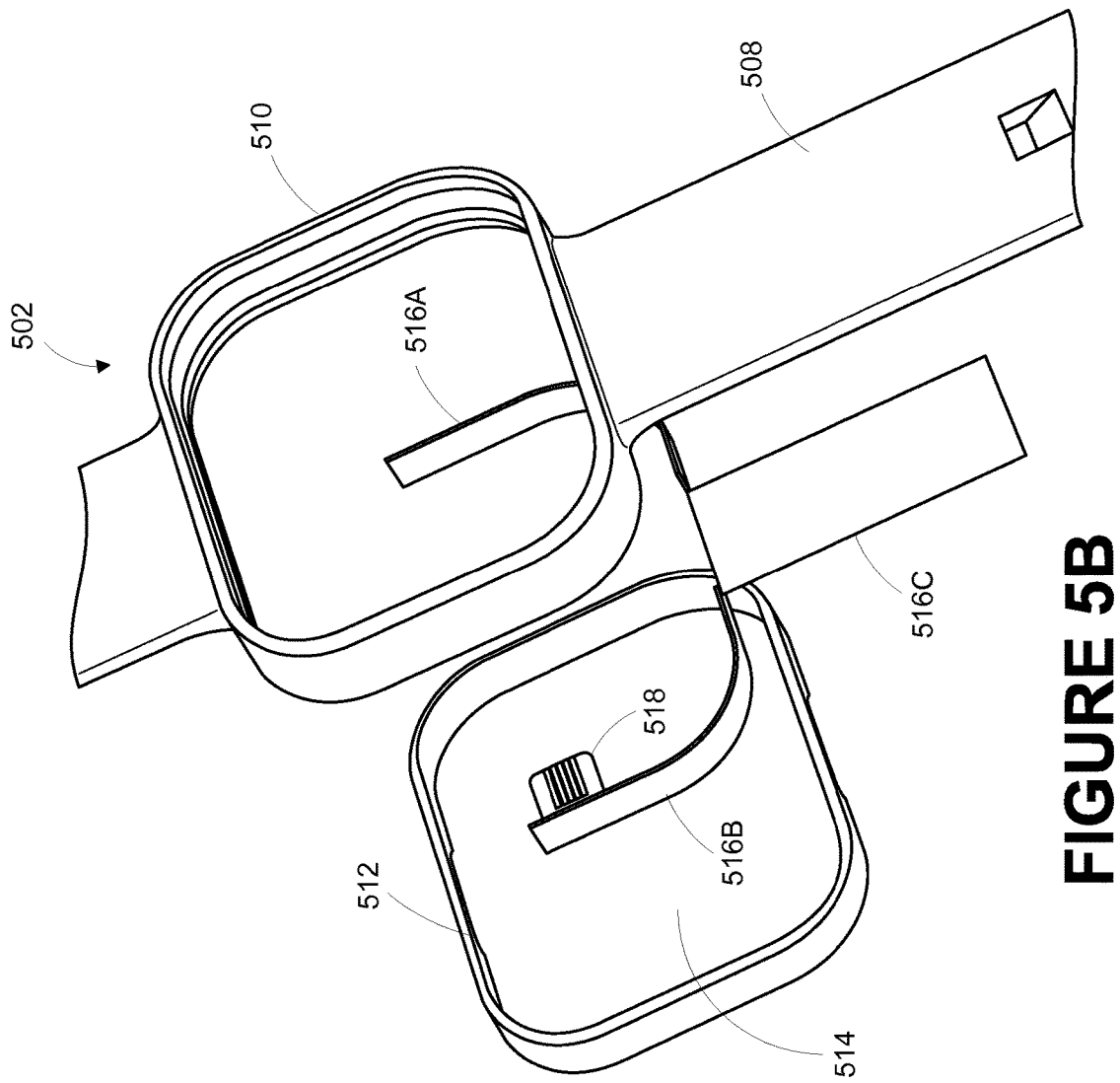
FIG. 5B illustrates an exploded view showing example components of a wrist band, in accordance with an example embodiment.

FIG. 5B illustrates an exploded view showing example components of the wrist band 502, in accordance with an example embodiment. The wrist band 502 may include a strap 508 that is configured for removable placement about a wrist of a wearer. The wrist band 502 may include a holder 510 coupled to the strap 508. The holder 510 defines a frame 512 that is configured to receive and secure the electronics module 500 within the holder 510. The frame 512 also defines an opening 514. When the wearable device is worn about a wrist, the biological sensor coupled to the electronics module 500 can be in contact with or proximate to skin of the wearer at a given wrist location through the opening 514. Thus, the sensor can measure a parameter via an external body surface proximate to the given wrist location.

Further, the wrist band 502 may include a flexible (non-rigid) printed circuit board (PCB) having three portions 516A, 516B, and 516C. Shapes and number of portions 516A, 516B, 516C of the flexible PCB as shown in FIG. 5B are examples for illustration only. Other configuration and shapes are contemplated for the flexible PCB. In examples, the flexible PCB is non-rigid so as to adapt to bending the strap 508 for example, when the wrist band is worn about a wrist of a wearer. The flexible PCB also allows, and is tolerant to, distortion to the strap 508, the holder 510, or the frame 512. The flexible PCB may be embedded within at least one of the holder 510 or the strap 508. For example, as shown in FIG. 5B, the portions 516A and 516B of the flexible PCB are embedded within the holder 510, and the portion 516C is embedded within the strap 508.

Figure 5C:
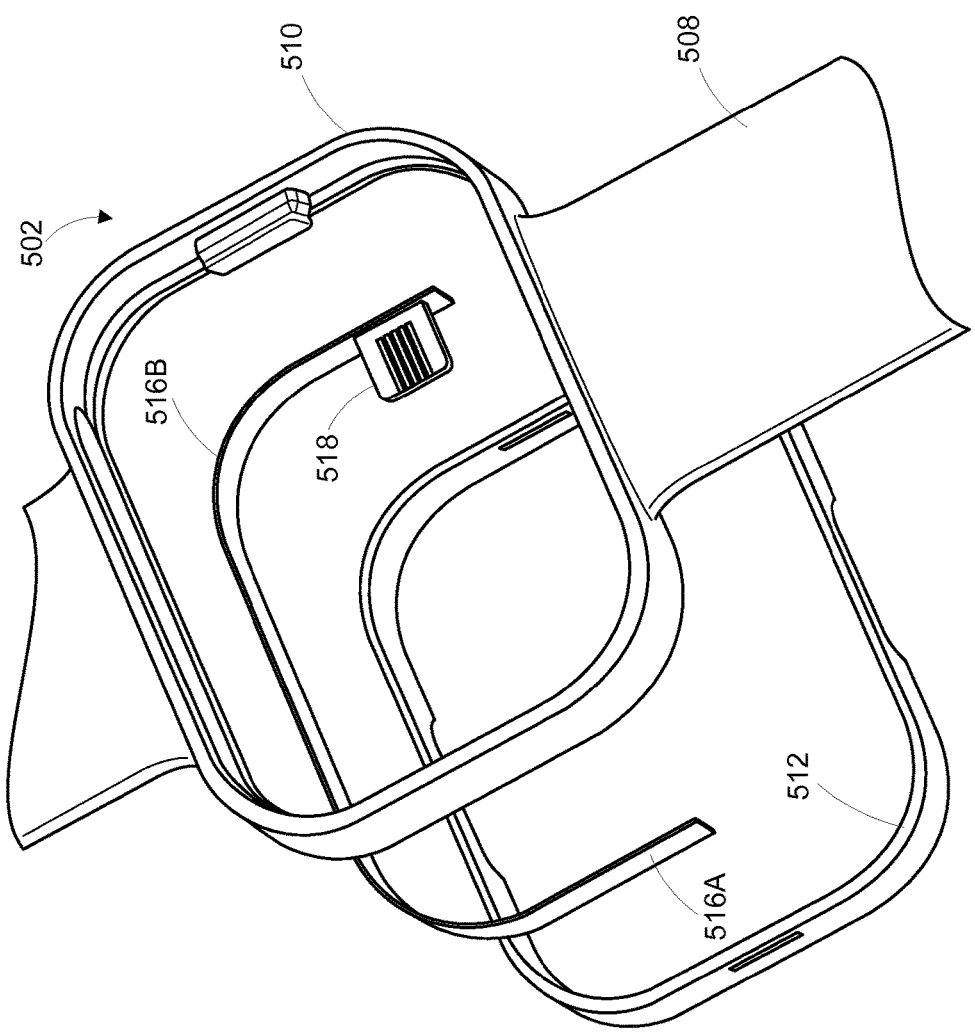
FIG. 5C illustrates the flexible PCB embedded in a holder, in accordance with an example embodiment.

FIG. 5C illustrates the flexible PCB embedded in the holder 510, in accordance with an example embodiment. As shown in FIG. 5C, the flexible PCB includes the two portions 516A and 516B embedded within the holder 510, and does not include the third portion 516C. In still other examples (not shown), the flexible PCB may be embedded with the strap without any portions in the holder 510.

The wrist band 502 may include other components that are not shown. For example, the wrist band 502 may also include an antenna coupled to, or in communication, with the flexible PCB. The wrist band 502 may include one or more biological sensors, or any type of sensors. The biological sensors coupled to wrist band 502 may be connected to the flexible PCB and configured to obtain measurements via the external body surface proximate to the wrist of the wearer when the wearable device is worn. Further, the wrist band 502 may also include a user interface that might include one or more of a display, buttons, touch screens/sensors, etc. that can be mounted on the holder 510 and/or the strap 508. The wrist band 502 may also include a respective rechargeable battery configured to power the flexible PCB and electronic components in communication with or coupled to the flexible PCB.

As shown in FIGS. 5B and 5C, the flexible PCB includes a connector 518. The connector 518 may be configured to electrically connect the flexible PCB to the communication port 504 (shown in FIG. 5A) when the electronics module 500 is received within the frame 512. The connector 518 may be any type of electrical connectors. For example, the connector 518 may be a Universal Serial Bus (USB) connector. However, any other type of connectors can be used.

Figure 5D:
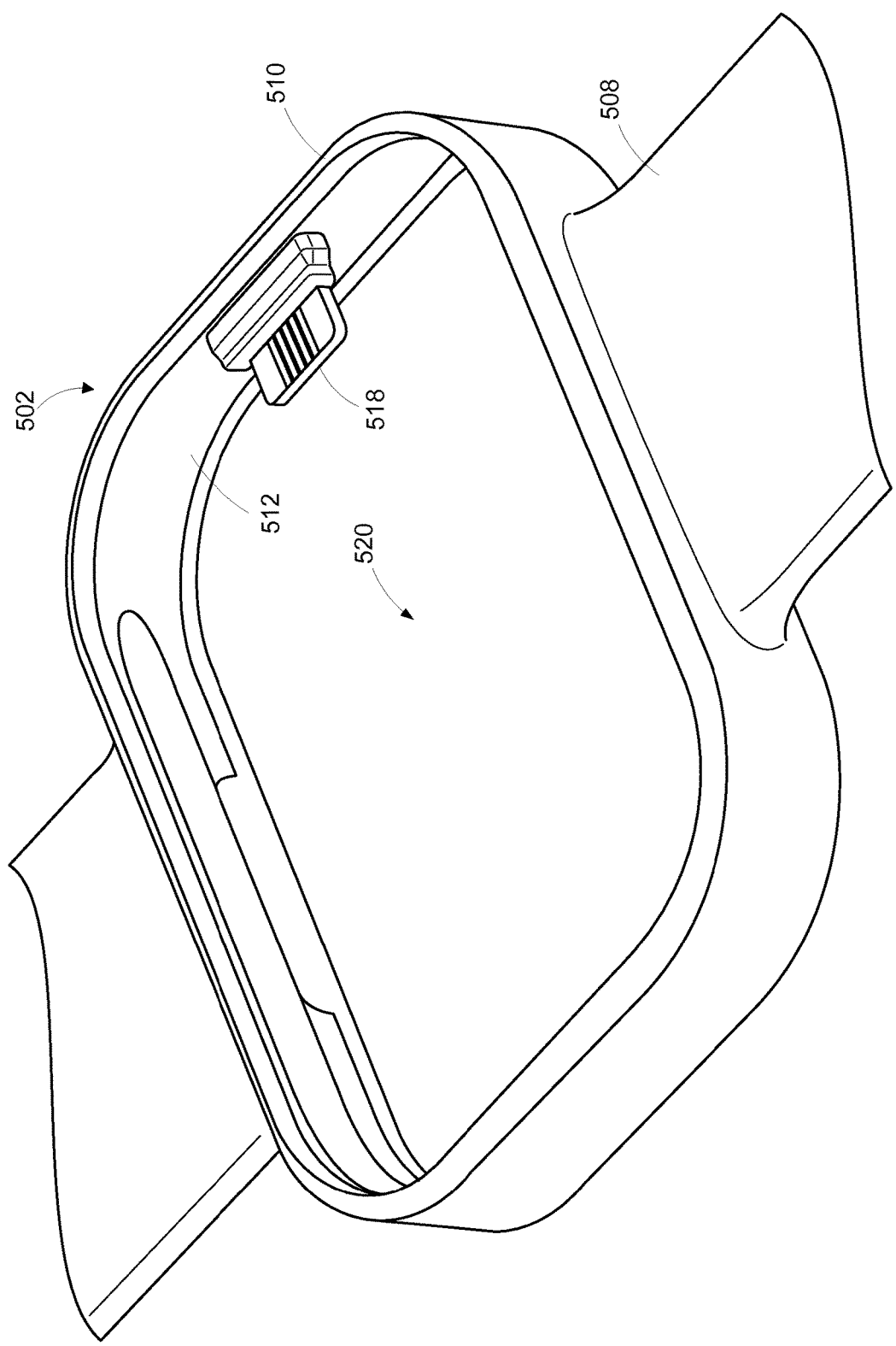
FIG. 5D illustrates an assembled wrist band, in accordance with an example embodiment.

FIG. 5D illustrates an assembled wrist band 502, in accordance with an example embodiment. As shown in FIG. 5D, the wrist band 502 forms a space 520 within the frame 512 that is configured to receive the electronics module 500.

Figure 5E:
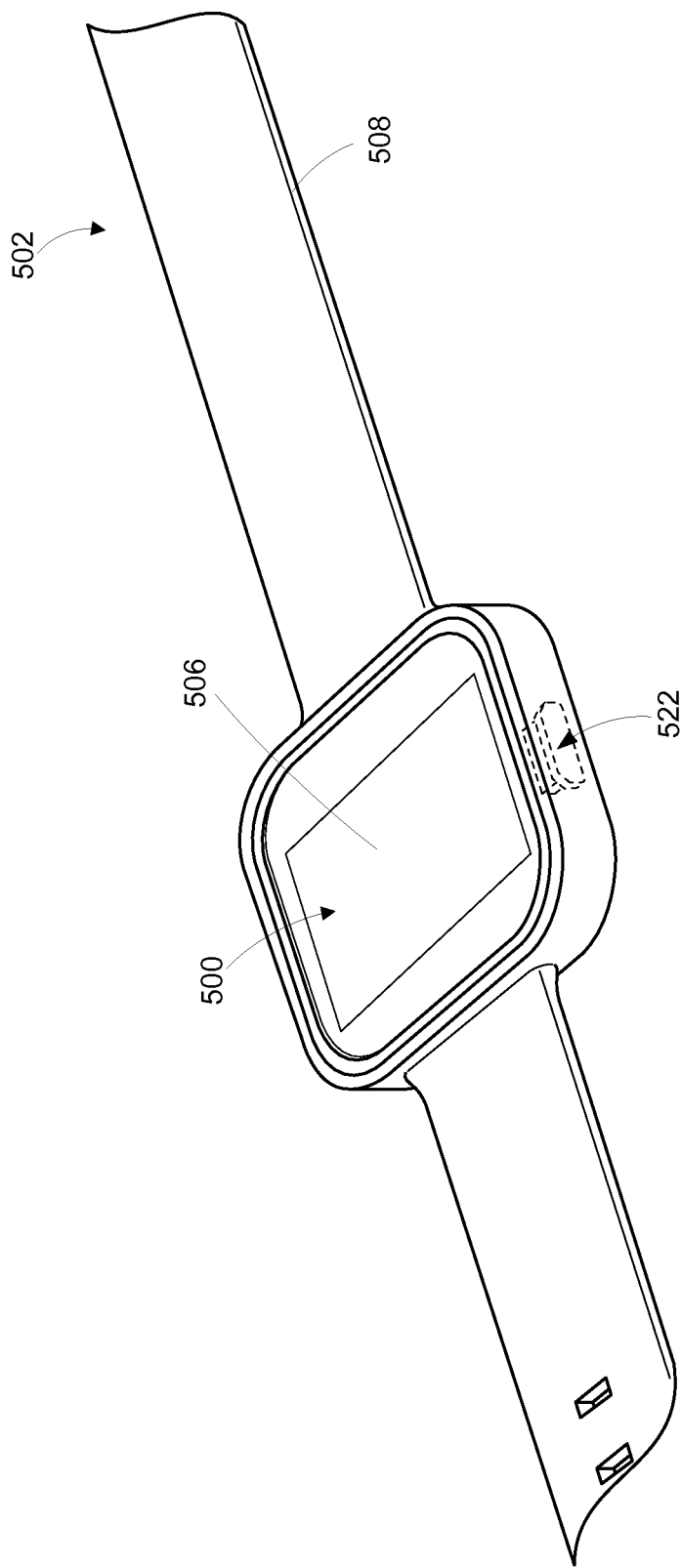
FIG. 5E illustrates an electronics module coupled to the wrist band, in accordance with an example embodiment.

FIG. 5E illustrates the electronics module 500 coupled to the wrist band 502, in accordance with an example embodiment. As shown in FIG. 5E, when the connector 518 is plugged into the communication port 504, the electronics module 500 is received and surrounded by the frame 512, and a connection 522 is made between the electronics module 500 and the flexible PCB. When the connection 522 is made, the flexible PCB becomes "live" and communicates with the electronics module 500 and components embedded therein. Thus, components of the wrist band 502 may communicate with respective components of the electronics module 500, and vice versa, via the connection 522. The connection 522 is shown as a physical connection in FIGS. 5B, 5C, and 5D (the physical connector 518 plugged into the communication port 504); however, in examples, the connection 522 may instead be wireless connection with no physical contact between the flexible PCB and the electronics module 500. Any type of wireless communication protocol can be used such as Bluetooth, ZigBee, WiFi, and/or some other wireless communication protocol.

The wrist band 502 extends or enhances functionality of the electronics module 500. As described above, the electronics module 500 may include basic functionalities and basic components that can be enhanced by being coupled to the wrist band 502. A plurality of wrist bands may be available, and the electronics module 500 can be coupled to any wrist band of the plurality of wrist bands based on a particular functionality associated with that wrist band.

As an example, sensor measurements obtained by the biological sensor coupled to the electronics module 500 may be transmitted to other devices or a server via an antenna coupled to the wrist band 502. In another example, a user interface may be coupled to the wrist band 502. In this example, the electronics module 500 may provide sensor information via the connection 522 to the wrist band 502 to provide a user-discernible indication of the sensor measurements to the wearer via the user interface. In another example, however, the electronics module 500 may provide the user-discernible indication via the display 506. In still another example, the wrist band 502 may include buttons and controls that can be used to provide user-inputs to the electronics module 500 via the connection 522. In yet still another example, as described above, the wrist band 502 may include a battery to power the flexible PCB and associated components. The battery of the wrist band 502 may be configured to provide power to the electronics module 500 when the battery of the electronics module 500 is depleted to extend period of time in which the electronics module 500 is active and functional. Similarly, the wrist band 502 may include a processor and data storage that can be used to enhance capability of the respective processor and the respective data storage of the electronics module 500. For instance, the data storage of the wrist band 502 may be used to store data communicated from the electronics module 500. As another example, the processor of the wrist band 502 may be configured to execute instructions in parallel with the processor of the electronics module 500 to enhance the capability (e.g., processing speed) of the wearable device.

The electronics module 500 can be unplugged and removed from the wrist band 502 and installed into a different wrist band that has a different functionality (e.g., a different biological sensor configured to make a different measurement associated with a given physiological parameter). In this manner, the same electronics module 500 can be plugged into different wrist bands to have different functionalities.

Figure 6:
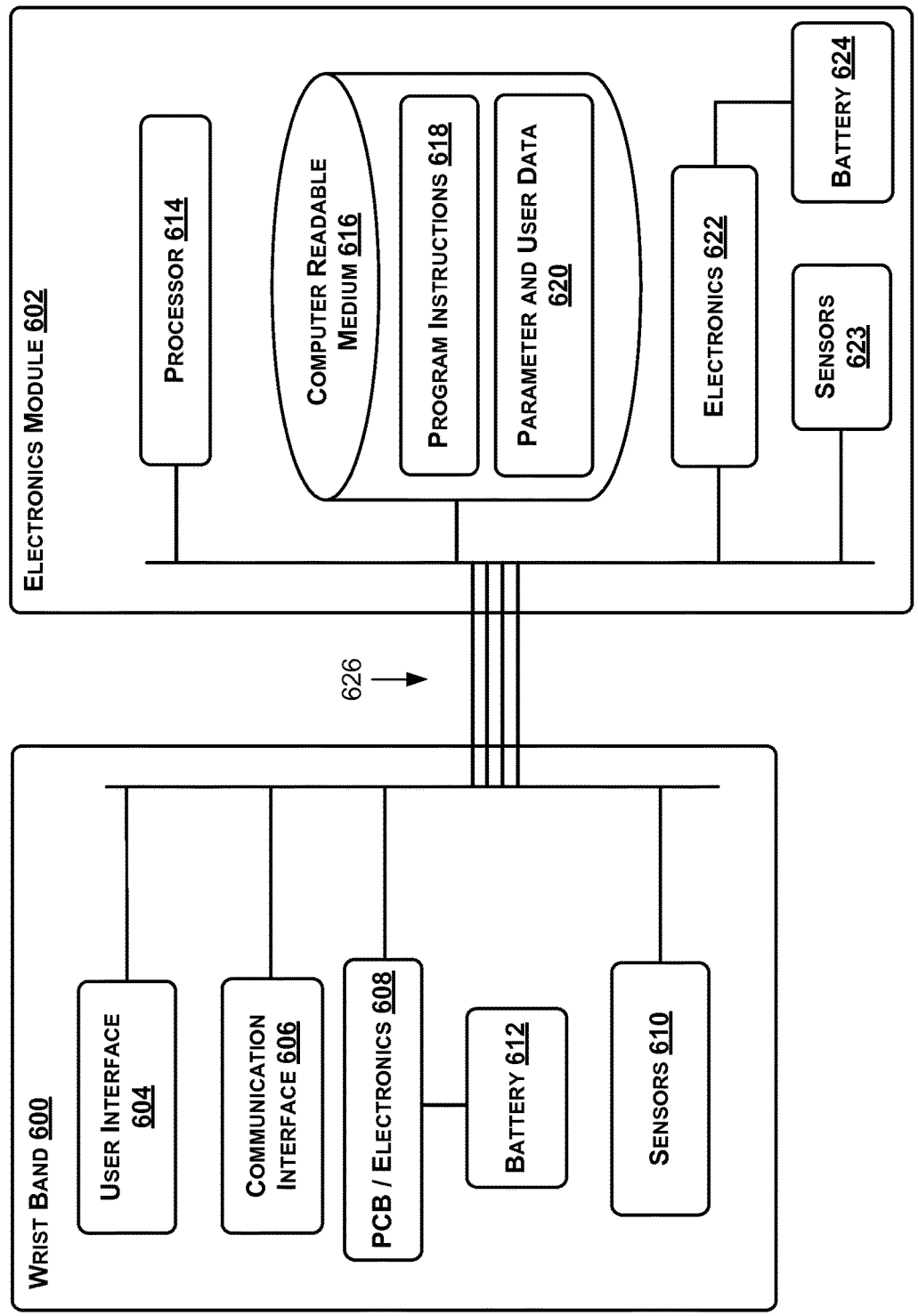
FIG. 6 is a functional block diagram of an example wearable device, in accordance with an example embodiment.

FIG. 6 is a functional block diagram of an example wearable device, in accordance with an example embodiment. The wearable device may take the form of or be similar to one of the wearable devices shown in FIGS. 1, 2A-B, 3A-3C, 4A-4C, and 5A-5E. However, the wearable device may also take other forms, for example, an ankle, waist, or chest-mounted device.

In particular, FIG. 6 shows an example of a wearable device having a wrist band 600 and an electronics module 602. The wrist band 600 includes a user interface 604, a communication interface 606, PCB (and associated electronics and components) 608, sensors 610, and battery 612. The electronics module 602 may include a processor 614, a computer readable medium 616 having stored thereon program instructions 618 and parameter and user data 620, electronics 622, sensors 623, and a battery 624 configured to power the electronics module 602. The wrist band 600 is coupled to the electronics module 602 via a connection 626. Components of the wrist band 600 may be in communication with respective components of the electronics module 602 through the connection 626. The connection 626 may be implemented via a physical connector (e.g., a USB connector) or a wireless connection via any type of wireless communication protocol.

The user interface 604 may include a display, buttons, controls, or any other input/output means. The communication interface 606 may include, for example, an antenna configured to send and receive information to and from other devices or servers via a network connection. The communication interface 606 can optionally include one or more oscillators, mixers, frequency injectors, etc. to modulate and/or demodulate information on a carrier frequency to be transmitted and/or received by the antenna. In some examples, the communication interface 606 may be configured to indicate an output from the processor 614 by modulating an impedance of the antenna in a manner that is perceivable by a remote server or other remote computing device.

The PCB 608 may be a flexible PCB similar to the flexible PCB described with respect to FIGS. 5A-5E. The PCB 608 may have various electronics components attached thereon or in communication therewith. The sensors 610 may include biological sensor configured to measure parameters related to galvanic skin response, for example, at an external surface of wearer proximate to a location where the wrist band 600 is mounted on the wearer's wrist. The battery 612 may be rechargeable battery configured to power components of the wrist band 600 such as the PCB 608 and the associated components.

The processor 614 may be a general-purpose processor or a special purpose processor (e.g., digital signal processors, application specific integrated circuits, etc.). The processor 614 can be configured to execute computer-readable program instructions 618 that are stored in a computer readable medium 616 and are executable to provide the functionality of a wearable device described herein.

The computer readable medium 616 may include or take the form of one or more non-transitory, computer-readable storage media that can be read or accessed by the processor 614. The computer-readable storage media can include volatile and/or non-volatile storage components, such as optical, magnetic, organic or other memory or disc storage, which can be integrated in whole or in part with the processor 614. In some examples, the computer readable medium 616 can be implemented using a single physical device (e.g., one optical, magnetic, organic or other memory or disc storage unit), while in other examples the computer readable medium 616 can be implemented using two or more physical devices.

The sensors 623 could include a GSR sensor, for example. The GSR sensor could be configured to obtain a measurement relating to the GSR of the skin at the external body surface. The battery 624 may be a rechargeable battery configured to power the electronics module 602 and all components associated therewith. If the battery 624 is depleted, the battery 612 of the wrist band 600 may be configured to power both the wrist band 600 and the electronics module 602. Conversely, if the battery 612 of the wrist band 600 is depleted, the battery 624 may be configured to power both the electronics module 602 and the wrist band 600. In some examples, the wearable device may include either the battery 612 or the battery 624, not both. For instance, the wearable device may include the battery 612 that is configured to power both the wrist band 600 and the electronics module 602.

The program instructions 618 stored on the computer readable medium 616 may include instructions to perform or facilitate some or all of the device functionality described herein. For instance, program instructions 618 could include instructions to operate the electronics 622 and the sensors 623 to make a GSR measurement (or any other type of measurement such as an optical measurement) via the sensors 623. The program instructions 618 could include instructions to operate based on the parameter and user data 620 stored in the computer readable medium 616 and/or modify the parameters and user data 620. For example, the parameters and user data 620 could include calibration data for the wearable device and/or stored GSR measurements made using the wearable device.

The program instructions 618 could further include instructions to determine the GSR based on calibration or other data stored in the parameters and user data 620. The instructions could include instructions to determine whether electronics module 602 is attached or coupled to the wrist band 600 and whether the wearable device was mounted to skin on an external surface of a wearer based on the measurement relating to the GSR.

The program instructions 618 could include instructions to make a plurality of measurements and/or determinations of the GSR at a plurality of points in time using the electronics 622 and the sensors 623. The program instructions 618 could include instructions to store measurements of the GSR in the parameters and user data 620 and/or later or update calibration or other data in the parameters and user data 620 based on measurements of the GSR or other factors.

The program instructions 618 stored on the computer readable medium 616 could include instructions for powering the electronics module 602 using the battery 624, or using the battery 612 when the battery 624 is depleted.

The program instructions 618 can include instructions for operating the user interface 604. For example, the program instructions 618 could include instructions for displaying a measured and/or determined GSR or other information generated by the electronics module 602, or for displaying one or more alerts generated by the electronics module 602 and/or received from an external system. Further, program instructions 618 may include instructions to execute certain functions based on inputs received via the user interface 604, such as inputs received via one or more buttons disposed on the user interface 604.

In some examples, GSR measurements, wearer profiles, history of wearable device use, health state information input by device wearers and generated recommendations and clinical protocols may additionally be input to a cloud network and be made available for download by a wearer's physician or other authorized recipient. Trend and other analyses may also be performed on the collected data, such as physiological parameter data and health state information, in the cloud computing network and be made available for download by physicians or clinicians.

Further, GSR measurements and health state data from individuals or populations of device wearers may be used by physicians or clinicians in monitoring efficacy of a drug or other treatment. Several wrist bands can be coupled to the electronics module 602 to implement different functionalities and obtain different measurements from different sensors. High-density, real-time data may be collected from a population of device wearers who are participating in a clinical study (or from different wrist bands coupled to the same electronics module 602 and worn by the same user) to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by instructions contained in the program instructions 618 that a medical condition is indicated, the electronics module 602 may generate an alert and communicate the alert through the connection 626 to the user interface 604. The alert may include a visual component, such as textual or graphical information displayed on a display, an auditory component (e.g., an alarm sound), and/or tactile component (e.g., a vibration). The textual information may include one or more recommendations, such as a recommendation that the wearer of the device contact a medical professional, seek immediate medical attention, or administer a medication.

Components of the wearable device illustrated in FIG. 6 may be configured to work in an interconnected fashion with each other and/or with other components coupled to respective systems. One or more of the described functions or components of the wearable device may be divided up into additional functional or physical components, or combined into fewer functional or physical components. In some further examples, additional functional and/or physical components may be added to the examples illustrated by FIG. 6.

IV. EXAMPLE METHODS

FIG. 7 is a flow chart of a method 700 of using a wearable device, in accordance with an example embodiment. The method 700 may include one or more operations, functions, or actions as illustrated by one or more of blocks 702-708. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

At block 702, the method 700 includes securing an electronics module within a holder coupled to a strap to form a wearable device. As described in FIGS. 5A-5E, the strap may be configured for removable placement about a wrist or any other external body surface. The electronics module includes a communication port and a biological sensor configured to obtain a measurement via an external body surface proximate to the wrist. The holder defines a frame configured to receive the electronics module, and the frame defines an opening through which the biological sensor can obtain the measurement via the external body surface. In an example, the external body surface may be proximate to the wrist. At least one of the strap and the holder includes a flexible PCB, where the flexible PCB includes a connector. Securing the electronics module within the holder includes electrically connecting the flexible PCB to the communication port by way of the connector. For instance, securing the electronics module to the holder is such that the frame surrounds the electronics module as shown in FIG. 5E.

In an example, the strap may further include an antenna in communication with the flexible PCB. The electronics module may be configured to communicate with the flexible PCB and the antenna via the connector. The electronics module may include a first rechargeable battery configured to power the electronics module, and the holder or the strap may include a second rechargeable battery configured to power the flexible PCB. If the first rechargeable battery is depleted, the second rechargeable battery may be configured to power the electronics module and the wrist band. Similarly, if the second rechargeable battery is depleted, the first rechargeable battery may be configured to power and wrist band and the electronics module. The electronics module may also include other components and sensors such as an accelerometer, a gyroscope, a location sensor, etc.

At block 704, the method 700 includes mounting the wearable device to the external body surface such that the opening is over the external body surface. The wearable device may be worn in a manner that positions the biological sensor proximate to a wrist location in preparation for obtaining a measurement by the biological sensor. In some examples, the wearable device could be configured to be mounted to a wrist of a wearer (e.g., the embodiments illustrated in FIGS. 1, 2A-B, 3A-C, 4A-B, 5A-5E) such that the sensor contacts skin of the wrist of the wearer. In some examples, the mount includes an adhesive, and mounting the wearable device to an external body surface includes activating, applying, and/or exposing the adhesive and adhering the wearable device to the external body surface.

At block 706, the method 700 includes causing the biological sensor to obtain one or more measurements via the external body surface. The biological sensor may be configured to obtain measurements when in contact with or proximate to the external body surface or skin about the wrist for example. The measurement may, for example, be associated with a GSR. In examples, the wrist band may also include one or more biological sensors (e.g., coupled to the strap and connected to the flexible PCB). The one or more biological sensors may be configured to obtain measurements related to or different from measurements obtained by the biological sensor of the electronics module.

At block 708, the method 700 includes receiving, from the wearable device, a user-discernible indication of the one or more measurements. In examples, the user-discernible indication may be provided by a display mounted on the holder or the strap of the wrist band. In another example, the user-discernible indication is provided by a user interface coupled to the electronics module. In examples, the electronics module may further provide sensor information related to the measurements obtained by the biological sensor, e.g., via an antenna coupled to the wrist band, to other computing devices and/or servers.

As described above, the wearable device described herein has a modular design allowing for coupling the same electronics module to different wrist bands. Thus, the electronics module may be removed from the holder (unplugged from the connector of the wrist band), and mounted to another holder of a different wrist band having different capabilities (e.g., different types of sensors configured to obtain different measurements via the external body surface).

Although the method 700 is described with respect to a band mounted on a wrist, the method 700 is also applicable to other forms of wearable device such as an ankle, waist, or chest-mounted wearable device.

V. CONCLUSION

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some examples may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how such information is used. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and how the collected information is used.

What is claimed is:

1. A wearable device, comprising:
   a strap;
   an electronics module comprising a communication port;
   a biological sensor electrically coupled to the electronics module;
   a holder coupled to the strap, wherein the holder defines a frame configured to receive the electronics module, wherein the frame defines an opening, wherein the strap is configured to mount the wearable device to an external body surface such that the opening is over the external body surface and the biological sensor is positioned to obtain a measurement via the external body surface through the opening, and wherein the frame has at least two sides bounding the opening, the at least two sides bounding the opening including two sides in contact with each other;
   a flexible printed circuit board (PCB) embedded within the holder and disposed in the two sides in contact with each other, such that the flexible PCB surrounds, at least partially, the opening defined by the frame; and
   a connector coupled to the flexible PCB and protruding into the opening defined by the frame, wherein the connector is configured to electrically connect the flexible PCB to the communication port when the electronics module is received in the frame.

2. The wearable device of claim 1, further comprising:
   an antenna in communication with the flexible PCB.

3. The wearable device of claim 1, wherein the external body surface is a wrist location.

4. The wearable device of claim 1, further comprising:
   a user-interface comprising at least a display mounted on the holder or the strap, wherein the display is configured to provide information associated with one or more measurements obtained by the biological sensor.

5. The wearable device of claim 1, further comprising:
   a rechargeable battery disposed in the holder or strap, wherein the rechargeable battery is configured to power (i) the flexible PCB and (ii) the electronics module.

6. The wearable device of claim 1, wherein the connector is configured to secure the electronics module within the holder such that the frame surrounds the electronics module.

7. The wearable device of claim 1, wherein the biological sensor is a first biological sensor, the wearable device further comprising:
   a second biological sensor connected to the flexible PCB, wherein the second biological sensor is able to obtain a different measurement via the external body surface.

8. The wearable device of claim 1, further comprising a user-interface configured to provide a user-discernible indication of the one or more measurements obtained by the biological sensor.

9. The wearable device of claim 1, wherein the electronics module further includes at least one of a motion sensor and a location sensor.

10. The wearable device of claim 1, wherein the electronics module further includes data storage and a touch sensor.

11. The wearable device of claim 1, wherein the electronics module includes the biological sensor.

12. The wearable device of claim 2, wherein the electronics module includes the antenna.

13. A wearable device, comprising:
   a strap;
   an electronics module comprising a communication port;
   a biological sensor electrically coupled to the electronics module;
   a holder coupled to the strap, wherein the holder defines a frame configured to receive the electronics module, wherein the frame defines an opening, wherein the strap is configured to mount the wearable device to an external body surface such that the opening is over the external body surface and the biological sensor is positioned to obtain a measurement via the external body surface through the opening, and wherein the frame has four sides bounding the opening, the four sides bounding the opening including two sides in contact with each other;
   a flexible printed circuit board (PCB) disposed in the two sides in contact with each other such that the flexible PCB surrounds, at least partially, the opening defined by the frame; and
   a connector coupled to the flexible PCB and protruding into the opening defined by the frame, wherein the connector is configured to electrically connect the flexible PCB to the communication port when the electronics module is received in the frame.

* * * * *